(12) United States Patent
Tedeschi

(10) Patent No.: US 7,470,281 B2
(45) Date of Patent: Dec. 30, 2008

(54) COATED STENT WITH CRIMPABLE COATING

(75) Inventor: Eugene Tedeschi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1258 days.

(21) Appl. No.: 10/133,156

(22) Filed: Apr. 26, 2002

(65) Prior Publication Data

US 2003/0204238 A1 Oct. 30, 2003

(51) Int. Cl.
*A61F 2/06* (2006.01)
(52) U.S. Cl. .................... 623/1.11; 623/1.42
(58) Field of Classification Search ............... 623/1.13, 623/1.42, 1.44, 1.46; 606/194
See application file for complete search history.

(56) References Cited

U.S. PATENT DOCUMENTS

| | | | |
|---|---|---|---|
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,697,967 A * | 12/1997 | Dinh et al. | 623/1.42 |
| 6,090,127 A | 7/2000 | Globerman | |
| 6,368,356 B1 * | 4/2002 | Zhong et al. | 623/1.18 |
| 6,371,982 B2 * | 4/2002 | Berg et al. | 623/1.13 |

FOREIGN PATENT DOCUMENTS

WO WO 00/45744 8/2000

* cited by examiner

*Primary Examiner*—Kevin T Truong
*Assistant Examiner*—Victor X Nguyen

(57) ABSTRACT

The expandable stent with a crimpable coating of the present invention provides an expandable stent with a coating containing a drug or therapeutic agent that can be crimped to a balloon according to conventional methods without damaging the coating. The stent comprises a stent frame, and a coating applied over the stent frame with the coating having at least one crimpable zone and containing a therapeutic agent. In one embodiment, the length of the crimpable zone can be much less than the length of the stent and the crimpable zone can have a higher durometer value than the remainder of the coating. In another embodiment, the coating in the crimpable zones can form rails to protect the coating in the regular coating zones.

18 Claims, 4 Drawing Sheets

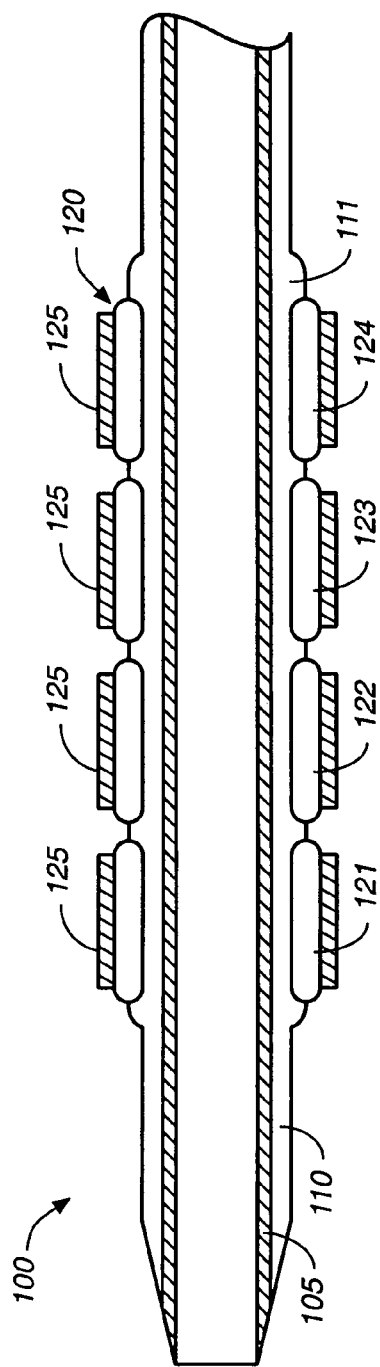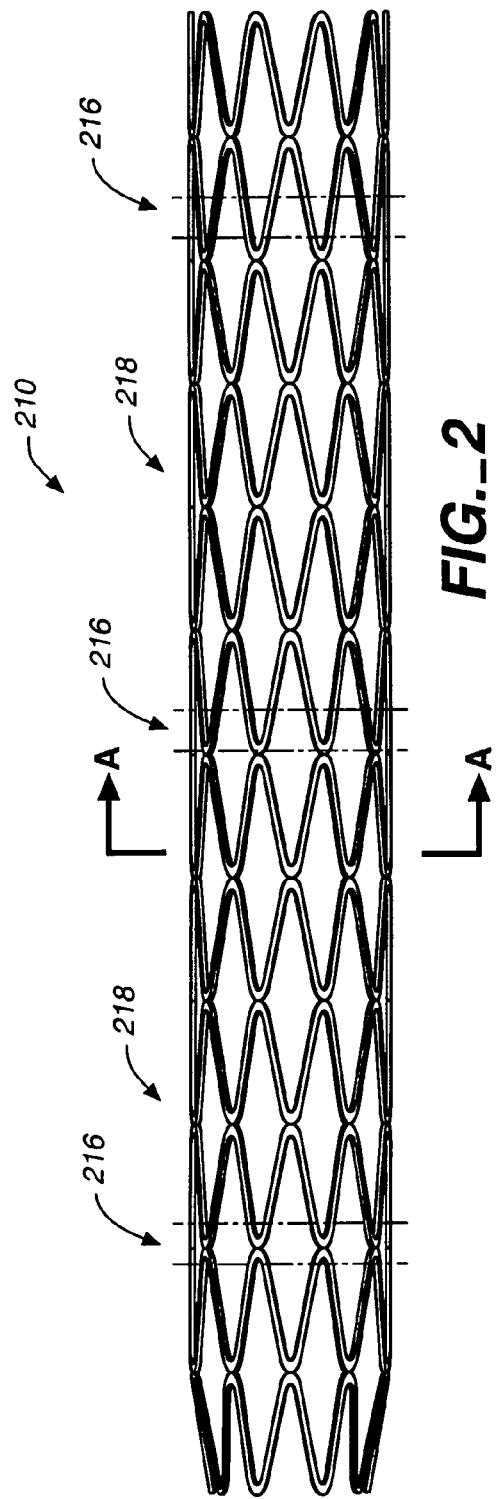

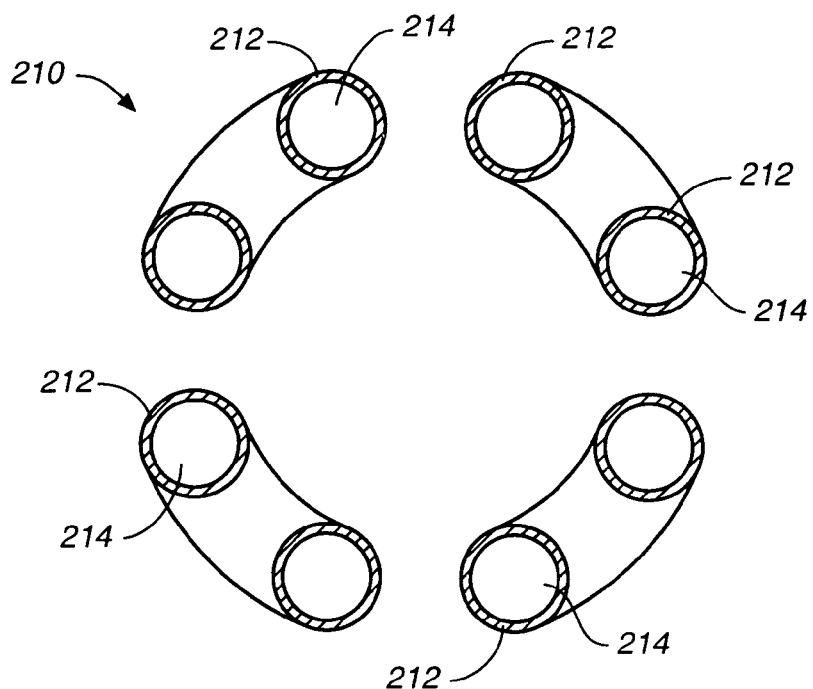
FIG._3 (Section AA)
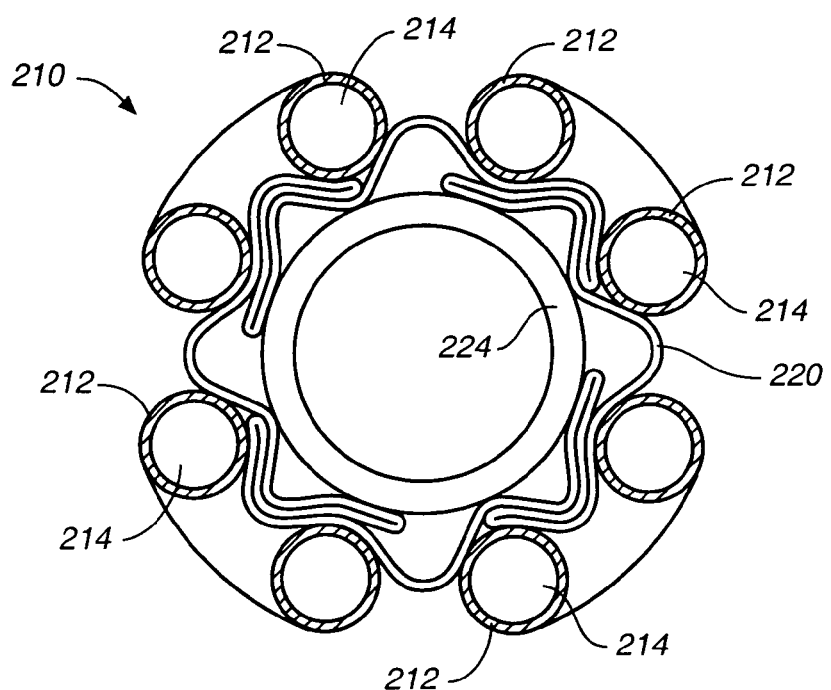
FIG._5 (Section BB)

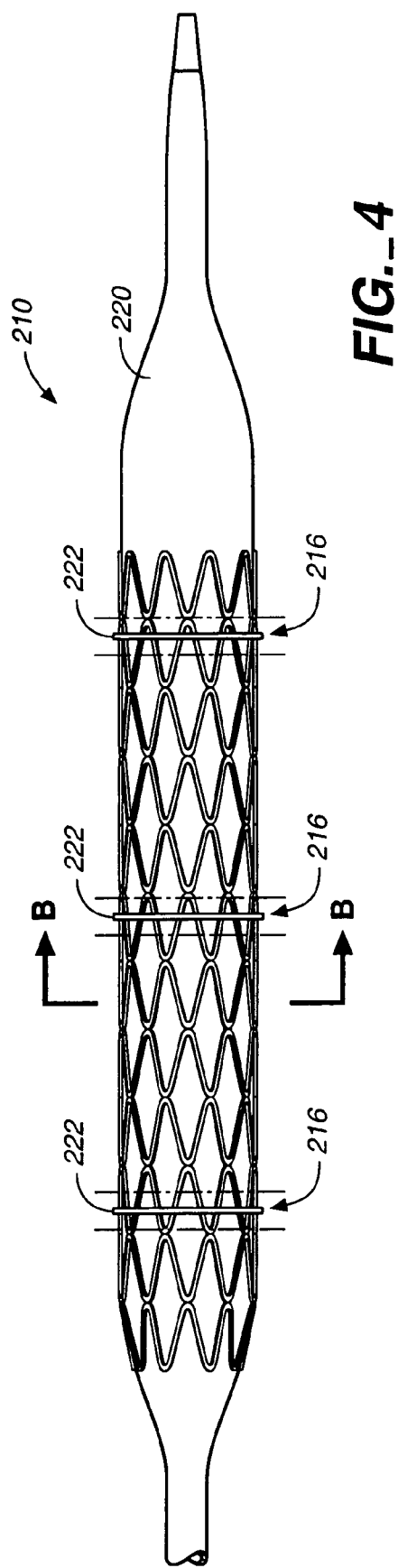
FIG._4
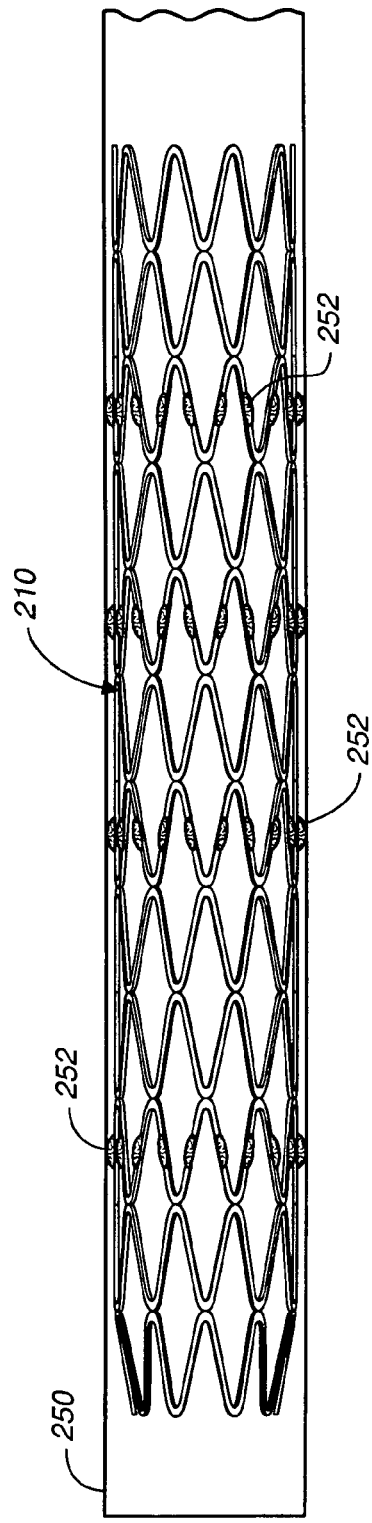
FIG._6

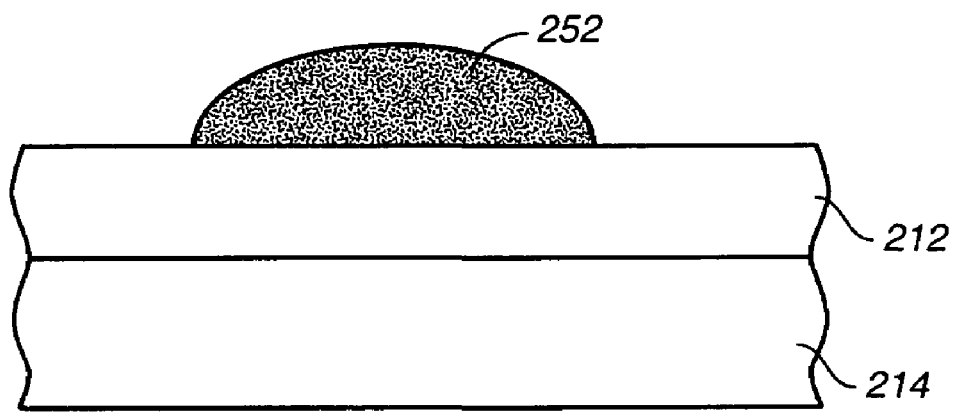
FIG._7
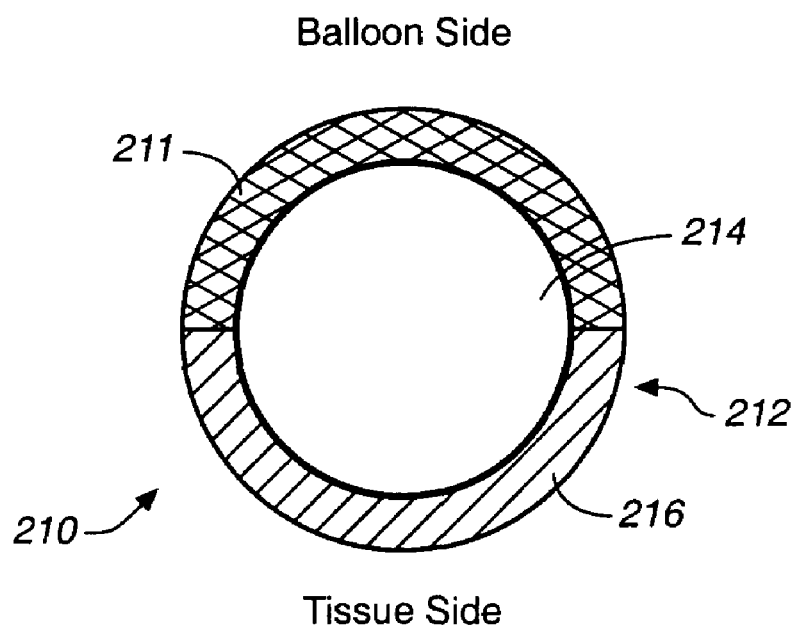
FIG._8

COATED STENT WITH CRIMPABLE COATING

TECHNICAL FIELD

The technical field of this disclosure is medical implant devices, particularly, an expandable stent with a crimpable coating.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents. Stents are typically installed with a reduced diameter and deployed to a final diameter. The stents can be self-expanding or can be expanded mechanically.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed.

During the procedure, the balloon stent catheter is advanced through a network of tortuous blood vessels. Furthermore, the balloon stent catheter also may encounter narrowed lumens or lumens that are obstructed. Once at the desired site, the balloon is inflated and expands the stent to a final diameter. After deployment, the stent remains in the vessel and the balloon catheter is removed.

The position of the stent on the balloon should be maintained while the balloon stent catheter is moved longitudinally through the network of vessels. In moving to the implant site, the stent may be shifted on the balloon so that the stent may not expand fully along its length or may be completely dislodged from the balloon. Current strategies for retaining the stent on the balloon include plastically deforming the stent so that it is crimped onto the balloon; increasing the friction forces between the stent and balloon by modifying the balloon through heat, pressure, or chemical or adhesive means; adding retainers that physically prevent the stent movement; and combinations thereof.

Stents have been developed with coatings to deliver drug or other therapeutic agents at the site of the stent. Typically, a coating of a soft polymer carrying the drug or therapeutic agent is applied to or bonded with the metal or other material forming the stent. Crimping the stent onto the balloon can damage the soft coating, either causing the coating at the crimp to be thinned or to be lost altogether. Any damage creates uncertainty about the dosage of drug delivered to the patient. Cost may increase because additional drug must be loaded to assure an effective dose. Crimping may also cause the coating material to adhere to the balloon, so that the coating material is withdrawn from the body when the balloon is withdrawn. Crimping force may have to be limited to protect the coating, which can limit the effectiveness of the crimp in holding the stent on the balloon.

WIPO International Publication No. WO 00/45744 to Yang et al. discloses a medical device, such as a stent, which includes a first coating including a drug or therapeutic substance and a relatively inelastic second coating impervious to the therapeutic substance, the second coating fracturing during expansion of the medical device to allow elution of the therapeutic substance through fissures formed through the second coating.

It would be desirable to have an expandable stent with a crimpable coating that would overcome the above disadvantages.

SUMMARY OF THE INVENTION

One aspect of the present invention provides a stent with a crimpable coating that maintains an effective coating after crimping.

Another aspect of the present invention provides a stent with a crimpable coating allowing application of sufficient crimping force to effectively attach the stent to the balloon.

Another aspect of the present invention provides a stent with a crimpable coating with the crimpable coating having a larger diameter than the remainder of the stent to act as a bearing rail for sliding against a compression sheath.

Another aspect of the present invention provides a stent with a crimpable coating with the coating staying on the stent rather than adhering to the balloon.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIG. 1 shows a stent delivery system made in accordance with the present invention.

FIGS. 2 & 3 show a perspective view and a cross section view, respectively, of a stent with a crimpable coating made in accordance with the present invention.

FIGS. 4 & 5 show a perspective view and a cross section view, respectively, of a stent with a crimpable coating crimped on a balloon catheter in accordance with the present invention.

FIGS. 6 & 7 show a perspective view and a detailed cross section view, respectively, of a stent with a crimpable coating including rails in accordance with the present invention.

FIG. 8 depicts a cross section of a stent element in which the coating has been hardened on the balloon or inner lumen side of the stent and left unhardened on the tissue side.

The FIGS. Are not necessarily to scale.

DETAILED DESCRIPTION OF THE PRESENTLY PREFERRED EMBODIMENT

The expandable stent with a crimpable coating of the present invention provides an expandable stent with a coating containing a drug or therapeutic agent that can be crimped to a balloon according to conventional methods without damaging the coating. The stent comprises a stent frame, and a coating applied over the stent frame with the coating having at least one crimpable zone and containing a therapeutic agent. In one embodiment, the length of the crimpable zone can be much less than the length of the stent and the crimpable zone can have a higher durometer value than the remainder of the coating. In another embodiment, the coating in the crimpable zones can form rails to protect the coating in the regular coating zones.

FIG. 1 shows a stent delivery system made in accordance with the present invention. The stent delivery system 100 includes a catheter 105, a balloon 110 operably attached to the catheter 105, and a stent 120 disposed on the balloon 110. The balloon 110, shown in a collapsed state, may be any variety of balloons capable of expanding the stent 120. The balloon 110 may be manufactured from any sufficiently elastic material such as polyethylene, polyethylene terephthalate (PET), nylon, or the like. In one embodiment, the balloon 110 may include retention means 111, such as mechanical or adhesive structures, for retaining the stent 120 until it is deployed. The catheter 105 may be any variety of balloon catheters, such as a PTCA (percutaneous transluminal coronary angioplasty) balloon catheter, capable of supporting a balloon during angioplasty.

The stent 120 may be any variety of implantable prosthetic devices capable of carrying a coating known in the art. In one embodiment, the stent 120 may have a plurality of identical cylindrical stent segments placed end to end. Four stent segments 121, 122, 123, and 124 are shown, and it will be recognized by those skilled in the art that an alternate number of stent segments may be used. The stent 120 includes at least one coating 125 carrying a therapeutic agent, which can be applied to the stent 120 by dipping or spraying the stent 120 with a coating liquid, or applying the coating liquid with a combination of methods. The coating can be applied as a liquid containing the drug or other therapeutic agent dispersed in a polymer/solvent matrix. In another embodiment, the therapeutic agent can be omitted from the coating and the coating included for its mechanical properties.

The coating 125 is merely exemplary, and it should be recognized that other coating configurations, such as multiple coating layers, are possible. Although the coating 125 is shown schematically on the outside of the stent 120, the coating 125 can be over the whole stent, both inside and outside.

FIG. 2 shows a perspective view of a stent with a crimpable coating made in accordance with the present invention and FIG. 3 shows a cross section of the stent of FIG. 2. The stent 210 is provided with a coating 212, which overlies a stent frame 214. The stent 210 can be divided into a plurality of zones, with crimpable zones 216 and regular zones 218. In another embodiment, a single crimpable zone can extend over the whole stent 210. The crimpable zones 216 provide areas where crimping pressure may be applied to crimp the stent 210 to a balloon without damaging the coating 212. In another embodiment, the crimpable zones 216 can have a larger diameter than the regular zones 218 to act as a bearing rail for sliding against a compression sheath, such as can be used with self-expanding stents.

The stent frame 214 of the stent 210 is conventional and can be made of a wide variety of materials, such as stainless steel, nitinol, MP35N, tantalum, glass, ceramic, nickel, titanium, aluminum, polymeric materials, or alloys or combinations of the above. The stent frame 214 can be formed through various methods as well. The stent frame 214 can be welded, molded, or consist of filaments or fibers which are wound or braided together in order to form a continuous structure. Typically, the stent 210 used for PTCA (percutaneous transluminal coronary angioplasty) to dilate a stenotic blood vessel has a crimped outer diameter in the range of typically 0.030 inches to 0.050 inches and is expanded to the appropriate diameter for the particular vessel, typically in the range of 2.25 millimeters to 5.0 millimeters. Given the progress of stent and catheter design, however, the above dimensions are merely for reference, and do not constitute a limitation to the usage of the current invention.

The coating 212 overlies the stent frame 214 and can be a polymer containing a drug or therapeutic agent. Once the stent 210 is inserted in a body, the therapeutic agent elutes from the polymer into the lumen or the surrounding tissue. The polymer can be biodegradable or non biodegradable, depending on the particular application. The coating 212 can be applied in a variety of conventional ways, including painting, spraying, dipping, wiping, electrostatic deposition, vapor deposition, epitaxial growth and other methods known to those of ordinary skill in the art. The coating 212 can typically be 2 microns to 20 microns in thickness, but can vary depending on the particular application, the particular polymer composition as well as the agents included therein. The coating 212 can also be formed of multiple layers of material to provide to provide different therapies as the individual layers become depleted or as different layers biodegrade. Different coatings can be applied on the inside and the outside of the stent 210 to provide different therapies on the lumen side and the tissue side of the stent 210. For ease of manufacture, the coating 212 can be applied only on the outside of the stent 210 to allow the stent 210 to be held in place by a mandrel inside of the stent 210 while the coating 212 is applied. The coating 212 may be uniform in thickness, or varied as desired.

The drug can also be varied between the crimpable zones 216 and the regular zones 218. For example, the coating 212 can be inert in the crimpable zone 216, so that no drug elutes from the crimpable zone 216. The coating 212 can contain a different drug dosage in the crimpable zone 216 than in the regular zone 218, such as a higher dose to account for reduced elution characteristics of the harder crimpable zone 216. The coating 212 can contain different drugs in the crimpable zone 216 than in the regular zone 218, such as a hydrophilic drug in one zone and a hydrophobic drug in the other zone. Those skilled in the art will appreciate that many combinations are possible.

The drug or therapeutic agent carried by the polymer of the coating 212 can be varied depending on the body lumen involved, the result desired, and the therapy indicated. Combinations of therapeutic agents can be used. Examples of therapeutic agents that can be used in the coating 212 are Resten-NG antisense compound, thrombin inhibitors, anti-thrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, anti-platelet agents, antimitotics, microtubule inhibitors, anti secretory agents, actin inhibitors, remodeling inhibitors, antisense nucleotides, anti metabolites, antiproliferatives, anti-cancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, and gene therapy agents.

The crimpable zones 214 can be manufactured by different methods. The crimpable zones 214 can have a durometer value in the range of about 90A to 70D, and typically in the range of about 40D to 50D. In one embodiment, the coating 212 can be applied uniformly of a single material, and the crimpable zones 214 treated, so that the coating 212 in the crimpable zones 214 transforms to a harder material. In another embodiment, a second coating layer can be applied over the uniform base coating layer in the crimpable zones 214, the second coating being a harder material to protect the underlying base coating layer. In yet another embodiment, a uniform second coating layer can be applied over the uniform base coating layer, then the crimpable zones 214 of the uniform second coating layer treated, so that the coating 212 in the crimpable zones 214 transforms to a harder material. These embodiments are exemplary only and those skilled in the art will appreciate that many combinations and treatments are possible within the spirit of the invention.

For the embodiment with a uniform coating treated in the crimpable zones, the coating 212 can be made of various polymers, such as amides, urethane acrylates, polyester acrylates, epoxy acrylates, acrylic acrylates, acrylate- terminated monomers and oligomers, and methacrylate-terminated monomers and oligomers. To be able to form the crimpable zones 214, the polymer must be able to undergo a change from an amorphous state to a more durable crystalline state under a hardening treatment.

The polymer must be strong enough in the crystalline state to withstand crimping without substantially cracking or deforming, so that the coating remains on the stent until the stent is deployed. Appropriate treatments, depending on the polymer, can be treatment with chemicals; heat; ultraviolet (UV) light, infrared (IR) light, or other frequency light; or gamma radiation, electron beam radiation, or other particle radiation. For example, the polymer coating can contain a photoinitiator, such as benzophenone, benzil dimethyl ketal, or 2-hydroxy-2methyl-1-phenyl-1-propanone, which will cross-link and harden the polymer when exposed to ultraviolet (UV) light. In another example, the polymer coating can be exposed to an electron beam, cross-link and harden the polymer without any photoinitiator required. In yet another example, the polymer can contain temperature-sensitive initiators such as peroxides or azonitrile compounds, which will cross-link and harden the polymer when heated. These treatments are exemplary only and other treatments will be well understood by those skilled in the art.

To selectively form the crimpable zones 214, several approaches are possible. In one approach, the coating can be completely uniform and treatment applied in particular areas, so that only those areas which become the crimpable zones are hardened. One example of this approach would be to have the whole coating contain a photoinitiator, mask the stent other than the crimpable zones, and expose the stent to light. Only the unmasked areas would harden to become the crimpable zones. The masking approach can also be used between the lumen and vessel side of the stent, so that the vessel side could be masked and the lumen side illuminated to harden the coating on the lumen side. In another approach, selected portions of the coating in the crimpable zones can contain an active agent such as a photoinitiator, so that the whole stent can be exposed to the light or other treatment, but only the portions of the coating containing the active agent will harden. The two approaches can be combined to produce detailed patterns, if desired.

For the embodiment with a uniform base coating layer with a second coating layer in the crimpable zones, the base coating layer can be made of various polymers, such as polycaprolactone, polylactide, polyglycolide, polyorthoesters, polyanhydrides, poly(amides), poly(alkyl 2-cyanoacrylates), poly(dihydropyrans), poly(acetals), poly(phosphazenes), poly(dioxinones), trimethylene carbonate, polyhydroxybutyrate, polyhydroxyvalerate, nonbiodegradable hydrophobic polymers, non-biodegradable hydrophilic polymers, polyolefins, polystyrene, polyester, polysulfide, polyurethanes, polyacrylates, silicone polymers, cellulose polymers, polyvinyl polymers, polyvinyl alcohol and derivatives, polyvinyl pyrolidone, polyethylene oxide, poly(hydroxy, aklymethacrylate), similar polymers, blends and copolymers and copolymers blends thereof, and combinations thereof, and the second coating layer can be made of various polymers, such as amides, urethane acrylates, polyester acrylates, epoxy acrylates, acrylic acrylates, acrylate-terminated monomers and oligomers, and methacrylate-terminated monomers and oligomers. The second coating layer needs to be compatible with the base coating layer and needs to adhere to the base coating layer to protect the base coating layer during crimping. To limit the second coating layer to the crimpable zones, the second coating layer can be applied in a controlled manner such that the second coating only contacts the crimpable zone, using a device such as a brush or fine spray nozzle the width of the crimpable zone, or applied more broadly with a coarse spray or by dipping, and a mask used to prevent coating the regular zone. In one embodiment, the second coating layer can be treated after application to increase hardness. The second coating layer must be strong enough to withstand crimping without substantially cracking or deforming, so that the coating remains on the stent until the stent is deployed. In one embodiment, the crimpable zone 216 can be hard and glassy, such as having about a 40D to 50D durometer value, so that the crimpable zone 216 cracks or checks when the stent 210 is expanded. The cracking can allow the therapeutic agent to more easily elute from the crimpable zone 216.

Referring to FIG. 6, the embodiment with a uniform base coating layer with a second coating layer in the crimpable zones can have additional advantages when used with a delivery sheath. FIG. 6 shows a stent with a crimpable coating including rails inside a delivery sheath. A delivery sheath 250 can be used around the stent 210 as the stent 210 is introduced into the body for deployment. For self-expanding stents, which expand without assistance when deployed, the delivery sheath 250 acts a compression sheath, which can be pulled back during deployment to allow the stent 210 to expand. The material in the second crimpable zone can be built up to a diameter greater than the diameter of the body of the stent 210 to form a rail 252. The rail 252 formed of the harder polymer contacts the delivery sheath 250, holding the rest of the stent 210 away from the delivery sheath 250 to protect the drug coating on the rest of the stent 210 before and during deployment. The inside surface of the delivery sheath 250 can be coated with a lubricity enhancing compound or coating, such as Photo Link® lubricity coating made by Sur Modix, Inc., Edenprairie, Minn. to further decrease the friction between the stent 210 and the delivery sheath 250.

FIG. 7 shows a detailed cross section of the embodiment of FIG. 6 in which the second crimpable zone provides a rail. The rail 252 stands above the surface of the coating 212, which can be applied over the stent frame 214 or additional coating layers. In one embodiment, the harder polymer forming the rail 252 can contain lubricity enhancing particles, such as Teflon® brand polytetrafluoroethylene or silicone, so that the stent 210 slides more easily within the delivery sheath 250.

Many variations on the coating and hardening process are possible. In one embodiment, the coating 212 can be hardened on both the tissue side and the lumen side of the stent 210. In yet another embodiment, the coating 212 can be hardened on the tissue side of the stent 210 and left unhardened on the lumen side. In yet another embodiment, particularly advantageous to avoiding damage of the coating by a balloon, the coating 212 can be hardened on the lumen side of the stent 210 and left unhardened on the tissue side. In another embodiment, the hardening of the crimpable zones 216 can be made reversible so the coating 212 in the crimpable zone 216 behaves like the coating in the regular zones 218.

FIG. 4 shows a perspective view of a stent with a crimpable coating crimped on a balloon catheter and FIG. 5 shows a cross section of the stent of FIG. 4. The stent 210 is crimped over the balloon 220 with a plurality of crimps 222. Each crimp 222 is located within one of the crimpable zones 216. The crimping does not substantially thin or remove the coating 212 over the stent frame 214. The balloon 220 is part of a balloon catheter that provides a connection so balloon 220 can be inflated from outside the body to expand the stent 210. A tube 224 provides a path for insertion of a conventional guide wire during installation of the stent 210.

The stent may be crimped in any location or locations as desired. For example, the stent 210 may be crimped every 2 mm along the axial length, but the interval can vary from 1 mm to 15 mm depending on the particular application. The crimps 222 can be made anywhere along the axial length where a crimpable zone 216 is present. In one embodiment, the crimping can be performed in the regions of the stent where it is easier to obtain a uniform coating, such as the regions away from where stent elements meet and away from weld regions. The crimping can be performed with conventional crimping tools as are used to crimp uncoated stents.

FIG. 8 depicts a cross section of a stent element 214 in which the coating 212 has been hardened on the balloon or inner lumen side of the stent 210 and left unhardened 216 on the tissue side. In this embodiment, the present invention is used less to create crimpable zones on the stent and more to decrease the likelihood the coated stent will adhere to the balloon. As understood, the balloon or inner lumen side of the stent element 214 contacts a balloon (best seen in FIG. 5.) such that the hardened coating 211 on that side decreases the likelihood the coating will adhere to the balloon material. Hardening may be accomplished using the process or processes set forth to create the crimpable zones discussed above.

It is important to note that FIGS. 1-8 illustrate specific applications and embodiments of the present invention, and are not intended to limit the scope of the present disclosure or claims to that which is presented therein. For example, the ability to provide patterns of hardened polymers on portions of the stent, as disclosed, can be used to provide protective areas on the stent where wear or damage of the coating is likely. The techniques used in protection of the crimpable zones also apply to protection of the coating where the stent contacts the balloon, the ends of the stent, and any other likely contact points. Moreover, while a representative stent structure is set forth, the coating having crimpable zones as set forth herein may be used on almost any coated metallic balloon-delivered stent design which is crimped about a balloon. The claims should not be interpreted as being only limited to the stent structure disclosed.

Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
a catheter;
a balloon operably attached to the catheter; and
a stent disposed on the balloon;
wherein the stent further comprises a stent frame and a coating applied to the stent frame, the coating having at least one crimpable zone, at least one regular zone, and containing a therapeutic agent.

2. The stent of claim 1 wherein the length of the crimpable zone is much less than the length of the stent and the crimpable zone has a higher durometer value than the remainder of the coating.

3. The stent of claim 2 wherein the durometer value of the crimpable zone is about 40 D-50 D.

4. The stent of claim 1 wherein the coating further comprises a polymer, the polymer selected from the group consisting of amides, urethane acrylates, polyester acrylates, epoxy acrylates, acrylic acrylates, acrylate-terminated monomers, oligomers, and methacrylate-terminated monomers and oligomers and combinations thereof.

5. The stent of claim 1 wherein the therapeutic agent is selected from the group consisting of pharmaceutical agents, radioactive agents, bioactive agents, and combinations thereof.

6. The stent of claim 1 wherein the therapeutic agent is selected from the group consisting of Resten-NG antisense compound, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix omponents, inhibitors, free radical scavengers, chelators, antioxidants, anti polymerases, antiviral agents, photodynamic therapy agents, gene therapy agents, and combinations thereof.

7. The stent of claim 1 wherein the stent is crimped to the balloon at the crimpable zone.

8. The stent of claim 7 wherein the stent is not crimped to the balloon at the regular zone.

9. The stent of claim 1 wherein the crimpable zone is harder than the regular zone.

10. A stent delivery system comprising:
a catheter;
a balloon operably attached to the catheter; and
a stent disposed on the balloon;
wherein the stent farther comprises a stent frame and a coating applied to the stent frame, the coating having at least one crimpable zone, at least one regular zone, and containing a therapeutic agent, the crimpable zone having sufficient hardness to maintain the coating on the stent frame after the stent is crimped on the balloon.

11. The stent delivery system of claim 10 wherein the length of the crimpable zone is much less than the length of the stent and the crimpable zone has a higher durometer value than the remainder of the coating.

12. The stent delivery system of claim 11 wherein the durometer value of the crimpable zone is about 40 D-50 D.

13. The stent delivery system of claim 10 wherein the coating farther comprises a polymer, the polymer selected from the group consisting of amides, urethane acrylates, polyester acrylates, epoxy acrylates, acrylic acrylates, acrylate-terminated monomers, oligomers, and methacrylate-terminated monomers and oligomers and combinations thereof.

14. The stent delivery system of claim 10 wherein the therapeutic agent is selected from the group consisting of pharmaceutical agents, radioactive agents, bioactive agents, and combinations thereof.

15. The stent delivery system of claim 10 wherein the therapeutic agent is selected from the group consisting of Resten-NG antisense compound, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, inhibitors, free radical scavengers, chelators, antioxidants, anti polymerases, antiviral agents, photodynamic therapy agents, gene therapy agents, and combinations thereof.

16. The stent of claim 10 wherein the stent is crimped to the balloon at the crimpable zone.

17. The stent of claim 16 wherein the stent is not crimped to the balloon at the regular zone.

18. The stent of claim 10 wherein the crimpable zone is harder than the regular zone.

* * * * *

UNITED STATES PATENT AND TRADEMARK OFFICE
CERTIFICATE OF CORRECTION

PATENT NO. : 7,470,281 B2 Page 1 of 1
APPLICATION NO. : 10/133156
DATED : December 30, 2008
INVENTOR(S) : Eugene Tedeschi It is certified that error appears in the above-identified patent and that said Letters Patent is hereby corrected as shown below:

Column 9, line 8,
"13. The stent delivery system of claim 10 wherein the coating farther comprises a polymer, the polymer selected from the group consisting of amides, urethane acrylates, polyester acrylates, epoxy acrylates, acrylic acrylates, acrylate-terminated monomers, oligomers, and methacrylate-ter-minated monomers and oligomers and combinations thereof."

should be changed to

-- 13. The stent delivery system of claim 10 wherein the coating further comprises a polymer, the polymer selected from the group consisting of amides, urethane acrylates, polyester acrylates, epoxy acrylates, acrylic acrylates, acrylate-terminated monomers, oligomers, and methacrylate-ter-minated monomers and oligomers and combinations thereof. --

Signed and Sealed this

Eighteenth Day of August, 2009

David J. Kappos
*Director of the United States Patent and Trademark Office*